US007475685B2

(12) United States Patent
Dietz et al.

(10) Patent No.: US 7,475,685 B2
(45) Date of Patent: Jan. 13, 2009

(54) METHOD AND DEVICE FOR DETECTING LEAKS IN RESPIRATORY GAS SUPPLY SYSTEMS

(75) Inventors: Florian Dietz, Lübeck (DE); Wolfgang Wedler, Hamburg (DE); Christof Göbel, Hamburg (DE)

(73) Assignee: Weinmann Geräte fär Medizin GmbH & Co. KG, Hamburg (DE)

( * ) Notice: Subject to any disclaimer, the term of this patent is extended or adjusted under 35 U.S.C. 154(b) by 519 days.

(21) Appl. No.: 10/550,634

(22) PCT Filed: Mar. 23, 2004

(86) PCT No.: PCT/EP2004/000607

§ 371 (c)(1),
(2), (4) Date: Sep. 22, 2005

(87) PCT Pub. No.: WO2004/084980

PCT Pub. Date: Oct. 7, 2004

(65) Prior Publication Data

US 2006/0249150 A1 Nov. 9, 2006

(30) Foreign Application Priority Data

Mar. 24, 2003 (DE) ............................. 103 13 082

(51) Int. Cl.
*A61M 11/00* (2006.01)
(52) U.S. Cl. ............................................... 128/204.23
(58) Field of Classification Search ..............................
128/204.21–204.23, 200.24, 203.27, 203.26,
128/204.18, 203.12, 207.14
See application file for complete search history.

(56) References Cited

U.S. PATENT DOCUMENTS

| 4,031,885 | A | | 6/1977 | Davis et al. | |
|---|---|---|---|---|---|
| 5,970,975 | A | * | 10/1999 | Estes et al. | 128/204.23 |
| 6,152,129 | A | | 11/2000 | Berthon-Jones | |
| 7,325,545 | B2 | * | 2/2008 | Dellaca' et al. | 128/204.23 |
| 2002/0014240 | A1 | | 2/2002 | Truschel | |

FOREIGN PATENT DOCUMENTS

| DE | 24 41 306 | 3/1975 |
|---|---|---|
| DE | 77 01 492 | 1/1977 |
| DE | 27 02 125 | 7/1978 |
| DE | 690 33 005 | 9/1999 |
| DE | 695 23 960 | 6/2002 |
| DE | 699 09 023 | 5/2004 |
| EP | 35 86 895 | 4/1993 |
| WO | 02/04057 | 1/2002 |
| WO | 02/20076 | 3/2002 |
| WO | 03/055552 | 7/2003 |

\* cited by examiner

*Primary Examiner*—Steven O Douglas
(74) *Attorney, Agent, or Firm*—Friedrich Kueffner (57) ABSTRACT

The invention relates to a method and a device for detecting leaks in respiratory gas supply systems. Both the pressure and the volume flow of the respiratory gas are detected and the relevant values are supplied to an evaluation device. The evaluation device is used to calculate both the respiratory parameter resistance and compliance and the leak for at least two successive breathing cycles. At least one control parameter with different signal amplitudes is pre-determined for the successive breathing cycles. The leak resistance is determined from the resulting differential sequences of pressure and flow for the successive breathing cycles.

29 Claims, 7 Drawing Sheets

METHOD AND DEVICE FOR DETECTING LEAKS IN RESPIRATORY GAS SUPPLY SYSTEMS

BACKGROUND OF THE INVENTION

1. Field of the Invention

The invention concerns a method for detecting leaks in ventilation systems, in which both the pressure of the respiratory gas and the volume flow of the respiratory gas are detected and fed into an evaluation unit.

The invention also concerns a device for detecting leaks in ventilators, which has both a system for detecting the pressure of the respiratory gas and a system for detecting the volume flow of the respiratory gas, and in which the detection systems are connected to an evaluation unit.

2. Description of the Related Art

In the performance of ventilation, various control methods for the ventilators are used. The devices are controlled mainly by means of automatic pressure control, so that a well-defined flow volume per respiratory cycle is not determined. Control of the device on the basis of volume control of the flow volume associated with a given respiratory cycle is also possible in principle but so far has been fraught with problems, because leaks can occur in the immediate area of the ventilator, in the area of the ventilation mask, and in the area of the connecting hose between the ventilator and the ventilation mask. Leaks can also occur in the area of contact between the ventilation mask and the patient's face. Total leakage losses from the complete ventilation system comprising these individual components are often on the order of 50% of the flow volume produced by the ventilator.

The previously known methods and devices for determining leakage losses are not yet sufficiently suitable for integration in an automatic control system for the device.

SUMMARY OF THE INVENTION

Therefore, the objective of the present invention is to improve a method of the aforementioned type in such a way that improved control of the device is supported.

In accordance with the invention, this objective is achieved by recording the respiratory parameters of pressure and flow for at least two successive respiratory cycles with the evaluation unit, by presetting at least one control parameter with different signal amplitudes for the successive respiratory cycles, and by determining resistance, compliance, and leak resistance from the resulting differential curves of pressure and flow for these respiratory cycles.

A further objective of the present invention is to design a device of the aforementioned type in such a way that volume-based control of the device is supported.

In accordance with the invention, this objective is achieved by designing the evaluation unit for determining the respiratory quantities of pressure and flow, by providing a storage device for at least one pair of value sequences of pressure and flow for a respiratory cycle, and by making it possible to generate at least one differential sequence for determining differential curves of compliance and resistance for at least two successive respiratory cycles.

On the basis of the determined leakage, it is possible to engineer the ventilator to supply an increased flow volume in such a way that, allowing for the leakage losses, a precisely defined useful volume flow is supplied. By taking the difference of the measured sequences of values of pressure and flow in two successive respiratory cycles, such that the selected control parameter has different control parameters in the respiratory cycles, it is possible to eliminate the effect of unknown quantities.

Direct leak detection for helping to achieve exact volume flow control is assisted by performing the computation for at least two immediately successive respiratory cycles.

To reduce the processing work, it is also possible to perform the computation for at least two respiratory cycles that are separated by at least one other respiratory cycle.

In accordance with a modification, different pressure levels are preset for the successive inspirations.

In particular, it is intended that the first pressure level be selected higher than the second pressure level.

In addition, it is also possible for the first pressure level to be selected lower than the second pressure level.

In accordance with another modification, it is also possible for different volume flows to be preset for the successive respiratory cycles.

In this modification as well, it is intended, in particular, that the first volume flow be preset higher than the second volume flow.

Moreover, it is also possible for the first volume flow to be preset lower than the second volume flow.

To guarantee that a preset desired value be maintained correctly on average, it is proposed that a large number of respiratory cycles, each with a varied control parameter, be carried out in such a way that the values of the control parameters are statistically distributed in such a way that a mean value corresponds to a preset desired value for the control parameter.

A closed-loop control system can be provided to carry out a leak compensation.

In particular, it is intended that the leak compensation is carried out dynamically.

To further support ventilation, it is proposed that a determination of the spontaneous respiratory behavior be performed by the evaluation unit.

In particular, it was found to be advantageous for the evaluation unit to compensate the effect of spontaneous respiratory behavior on the ventilation.

In a typical embodiment, leak detection is carried out in an area between a ventilator and a patient.

In accordance with another modification, it is proposed that the measurements be carried out only during inspiratory phases of the respiratory cycles.

To detect the ventilation pressure, it is proposed that at least one pressure sensor be connected to the evaluation unit.

Ventilation flow can be detected by connecting at least one volume flow sensor to the evaluation unit.

The arrangement of at least one of the sensors so that it faces a ventilator that is supplying the respiratory gas is conducive to a compact design of the device.

Improved measuring accuracy can be obtained by arranging one of the sensors so that it faces a ventilation mask.

In a typical embodiment, an expiration valve is arranged so that it faces the ventilation mask.

The arrangement of a discharge system so that it faces the ventilator also contributes to a compact design of the device.

In clinical applications, it is possible for a patient interface that is connected with the ventilator by the respiratory gas hose to be designed as an invasive device.

In particular, however, it is intended that a patient interface that is connected with the ventilator by the respiratory gas hose be designed as a noninvasive device.

In one embodiment of a signal generator, the evaluation unit has an amplitude generator for a pressure that varies from respiratory cycle to respiratory cycle.

In accordance with another embodiment, it is provided that the evaluation unit has an amplitude generator for a volume flow that varies from respiratory cycle to respiratory cycle.

Specific embodiments of the invention are shown schematically in the drawings.

DESCRIPTION OF THE PREFERRED EMBODIMENTS

Figure 1:
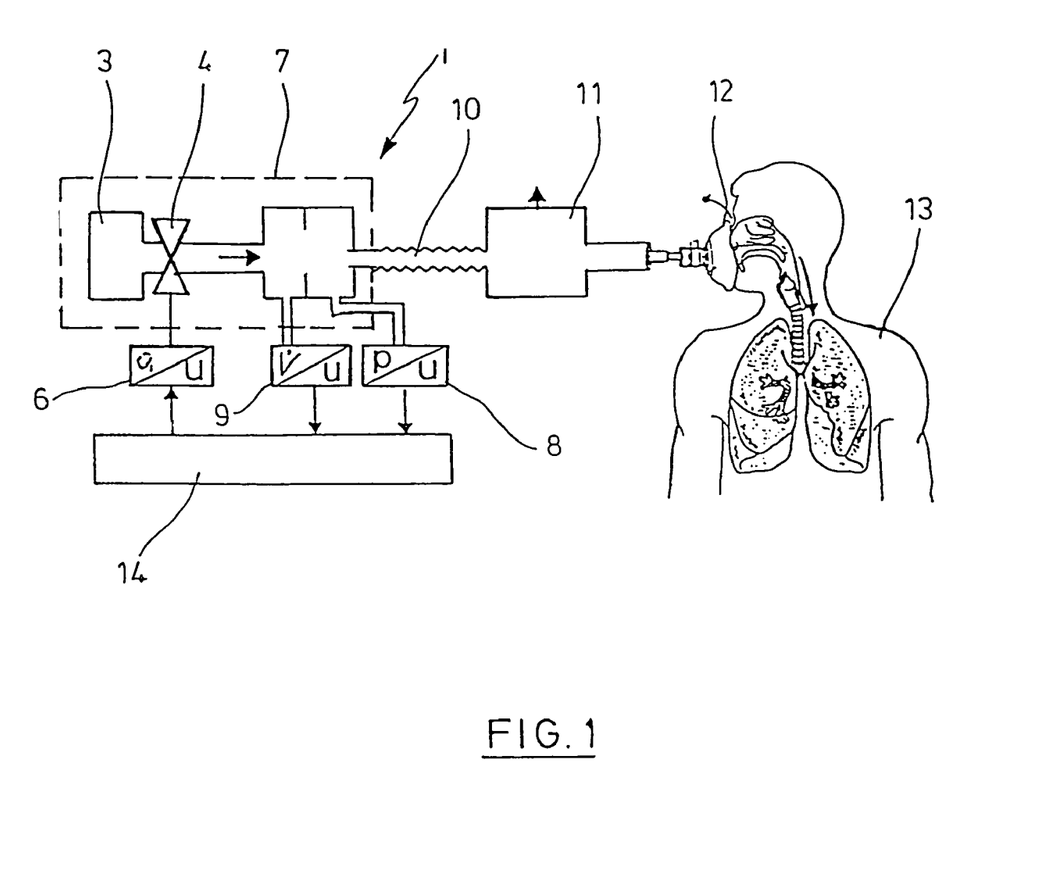
FIG. 1 shows a functional block diagram of the device illustrating its essential components.

In the embodiment shown in FIG. 1, a ventilation system 1 has a driven fan 3. The fan 3 is driven by a motor or some other power source. The fan 3 is connected to a control valve 4, which has a control unit 6 and transforms a control voltage to an associated valve position.

In the illustrated embodiment, a pressure sensor 8 and a volume flow sensor 9 are connected to a ventilator 7, which consists essentially of the fan 3 and the control valve 4. The volume flow sensor 9 is typically designed as a differential pressure sensor, whose signal is converted to an associated volume flow.

The ventilator 7 is connected by a respiratory gas hose 10 and an expiration valve 11 to a ventilation mask 12, which can be positioned over the face of a patient 13.

The sensors 8, 9 are connected to an evaluation unit 14, which in turn is connected to the control unit 6.

Figure 2:
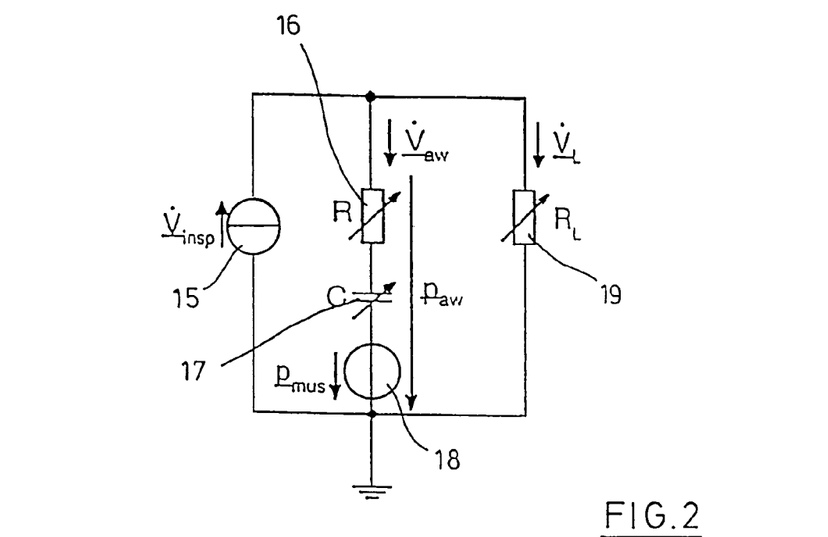
FIG. 2 shows an electrical circuit diagram analogous to the lung of a patient, which is considered as a model in the control of the device.

FIG. 2 shows an equivalent electrical circuit diagram, which reproduces the function of the lung of the patient 13 and is used in the evaluation unit 14 as a model for performing the computations. A volume flow generated by a volume flow source 15 is supplied to the parallel connection of two flow branches. One of the branches contains the series connection of the resistance 16 and the compliance 17 and a source of interference 18, which generates an additional volume flow and represents possible activity of the patient 13 himself. The second flow branch contains a leakage resistance 19.

The equivalent electrical circuit diagram of the respiratory tract according to FIG. 2 shows that the pressure $P_{mus}$ of a patient produced by his active breathing activity contributes to the airway pressure $P_{aw}$ and thus to the flow into the lung $V'_{aw}$. Accordingly, leak identification must also take $P_{mus}$ into account if the leakage flow $V'_L$ is to be adequately compensated.

Assuming that the respiratory effort of the patient between inspirations varies by only an insignificant amount, the respiratory effort component can be eliminated by subtraction. The following relationship in the complex variable domain of the Laplace transform is obtained from the equivalent circuit diagram according to FIG. 2 for the airway pressure $P_{aw}$ and the inspiratory flow $V'_{insp}$:

$$P_{aw}(s) = [P_{mus}(s) + V'_{insp}(s)(1+sRC)/sC] \times sR_L C/(1s(R+R_L)C)$$

The differences of the airway pressure $\Delta p_{aw}$ and the inspiratory flow $\Delta V'_{insp}$ are computed as follows:

$$\Delta P_{aw}(s) = P_{aw,k}(s) - P_{aw,k1}(s)$$

$$\Delta V'_{insp}(s) = V'_{insp,k}(s) - V'_{insp,k1}(s)$$

where k is the running number of the inspiration.

Assuming that the respiratory effort with respect to time is the same in successive inspirations, i.e., assuming that $$P_{mus,k}(s) = P_{mus,k1}(s)$$

a simpler relationship is obtained between the pressure difference $\Delta p_{aw}$ and the flow difference $\Delta V'_{insp}$ in the complex variable domain of the Laplace transform:

$$\Delta P_{aw}(s) = \Delta V'_{insp}(s)(1+sRC)R_L/(1+s(R+R_L)C)$$

To reconstruct the behavior of $P_{mus}$, the inversion of the first equation must be used. To this end, the identified estimated values are used as parameters, and the measured values are accounted for.

$$P\hat{}_{mus}(s) = (1+s(R\hat{}+R\hat{}_L)C\hat{})/sR\hat{}_L C\hat{} P_{FS}(s) - (1+sR\hat{}C\hat{})/sC\hat{} V'_{FS}(s)$$

A reconstruction of this type allows an evaluation of the spontaneous respiration and thus indirectly an evaluation of the quality of ventilation. In the simplest case, it can be decided by integration of the reconstructed values whether the patient is breathing with or against. For the first time, more complicated methods of classification can derive from this a decided evaluation for the volume-controlled ventilation, for example, with respect to synchronization or the level of respiratory effort.

Figure 3:
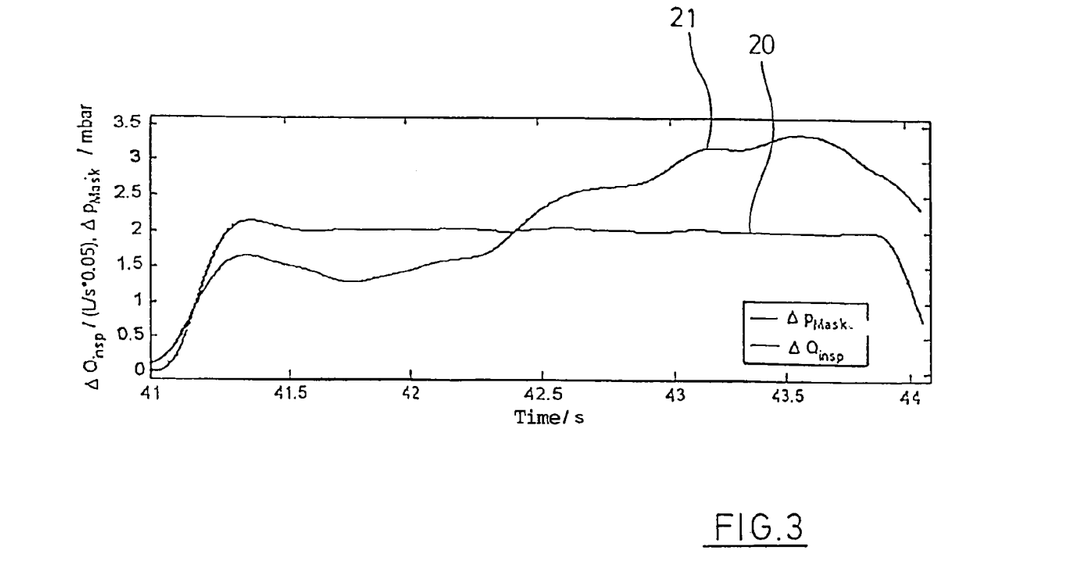
FIG. 3 shows a graph that illustrates the differences of measured quantities between two inspirations.

FIG. 3 shows the behavior with respect to time of the difference of the measured quantities between two respiratory cycles, one being an inspiratory volume flow difference 20, and the other being a pressure difference 21 in the area of the ventilation mask 12.

Figure 4:
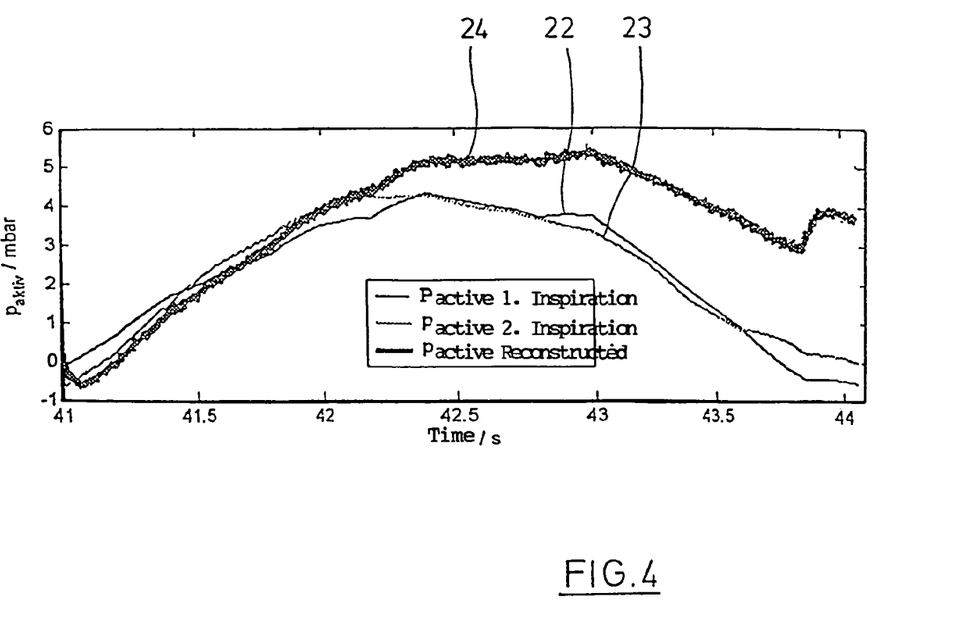
FIG. 4 shows a graph for the reconstruction of the course with respect to time of spontaneous respiration with evaluation of the difference values with respect to pressure and volume flow during two inspirations with different inspiratory volume flows.

FIG. 4 shows, with respect to a first pressure curve 22 for a first respiratory cycle and a second pressure curve 23 for a second respiratory cycle, the determined reconstruction curve 24 for spontaneous respiration of the patient 13, taking into account the volume flow difference 20 and the pressure difference 21 between two inspirations with different inspiratory volume flows.

Figure 5:
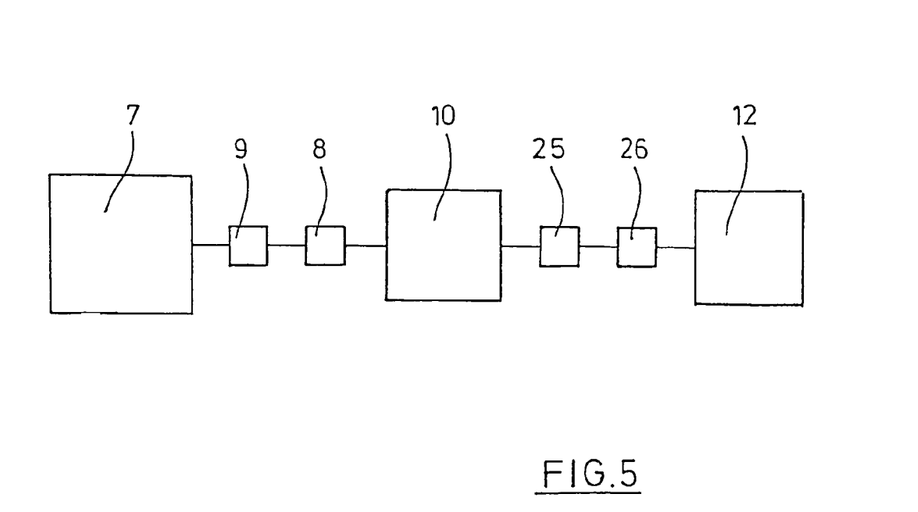
FIG. 5 shows a functional block diagram for illustrating the design of the device.

FIG. 5 shows the device illustrated in FIG. 1 in the form of a functional block diagram. The ventilator 7 is connected to a respiratory gas hose 10, and the volume flow sensor 9 and the pressure sensor 8 are arranged in the area between the ventilator 7 and the respiratory gas hose 10. The respiratory gas hose 10 is connected to the ventilation mask 12, and an additional volume flow sensor 25 and an additional pressure sensor 26 are positioned in the area between the respiratory gas hose 10 and the ventilation mask 12. As an alternative to the illustration in FIG. 5, the sensors can also be arranged only in the area between the ventilator 7 and the respiratory gas hose 10 or only in the area between the respiratory gas hose 10 and the ventilation mask 12. Naturally, a setup with a mass flowmeter is also possible; and in this case, a conversion to volume flow is made.

Figure 6:
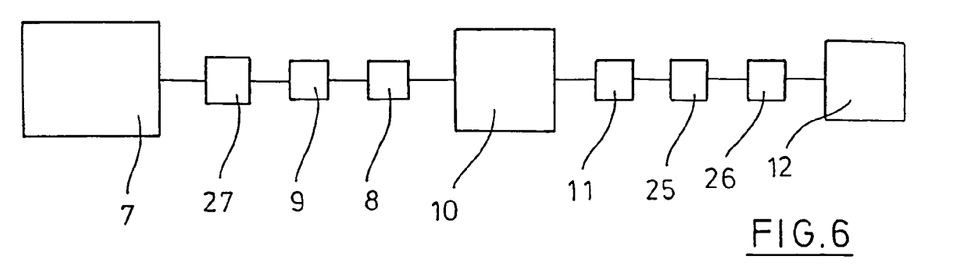
FIG. 6 shows a functional block diagram of a modified design of the device.

In accordance with the embodiment shown in FIG. 6, an expiration valve 11 is arranged in the area between the respiratory gas hose 10 and the ventilation mask 12, and a discharge system 27 is arranged between the ventilator 7 and the respiratory gas hose 10. It is also possible to arrange only the expiration valve 11 in the area between the respiratory gas hose 10 and the ventilation mask 12 or to arrange only the discharge system 27 in the area between the ventilator 7 and the respiratory gas hose 10. Furthermore, it is possible to replace the expiration valve 11 with a discharge system 27 and the discharge system 27 with an expiration valve 11.

As an alternative to the ventilation mask 12 shown in the specific embodiments, other noninvasive devices can be used to provide a connection with the patient 13. For example, the use of masks or headpieces is possible. A connection between the ventilation system 1 and the patient 13 can also be established by invasive coupling devices, for example, an intubation tube, a tracheostoma, or a laryngeal mask.

The ventilation systems that are used can be designed for carrying out various types of ventilation, for example, control mode ventilation, assist/control mode ventilation, or assist mode ventilation. In addition, the method can be used in periodic breathing and for CPAP ventilation or APAP ventilation.

The determination of resistance and compliance can be made, for example, exclusively during the inspiratory or exclusively during the expiratory time intervals of the respiratory cycles. However, it is also possible to make these determinations during both the inspiratory and expiratory phases.

Figure 7:
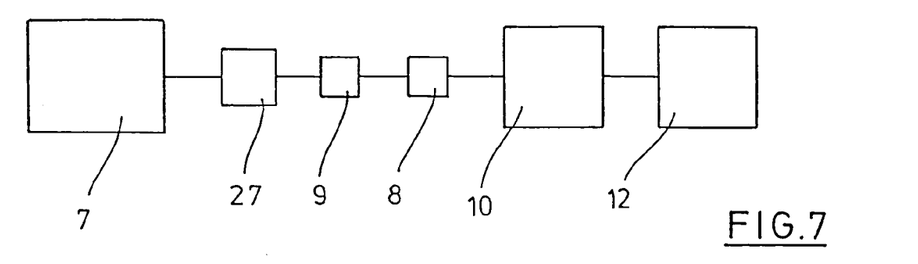
FIG. 7 shows another modification of the design of the device.

FIG. 7 shows the previously mentioned embodiment, in which the respiratory gas hose 10 is directly coupled with the ventilation mask 12, and the discharge system 27 and the sensors 8, 9 are positioned only in the area between the ventilator 7 and the respiratory gas hose 10.

Figure 8:
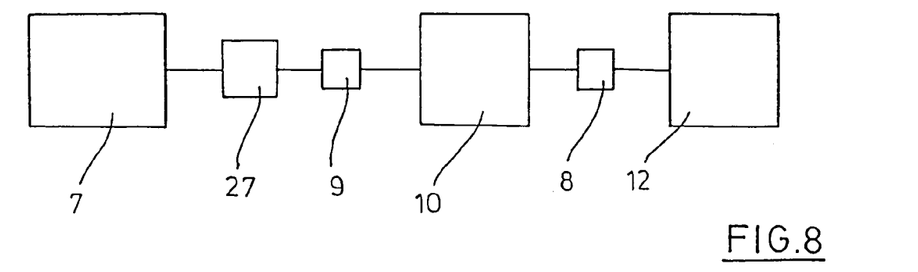
FIG. 8 shows a functional block diagram of another modified design of the device.

FIG. 8 shows an embodiment that is a modification of the embodiment shown in FIG. 7, in which the discharge system 27 and the volume flow sensor 9 are positioned between the ventilator 7 and the respiratory gas hose 10, and the pressure sensor 8 is positioned between the respiratory gas hose 10 and the ventilation mask 12.

Figure 9:
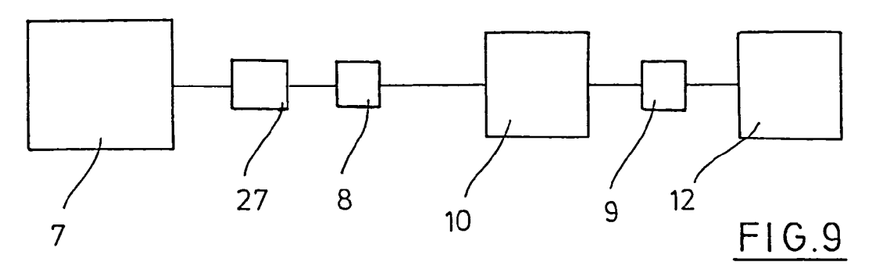
FIG. 9 shows another modification of the device.

In the embodiment in FIG. 9, the discharge system 27 and the pressure sensor 8 are positioned between the ventilator 7 and the respiratory gas hose 10, and the volume flow sensor 9 is positioned between the respiratory gas hose 10 and the ventilation mask 12.

Figure 10:
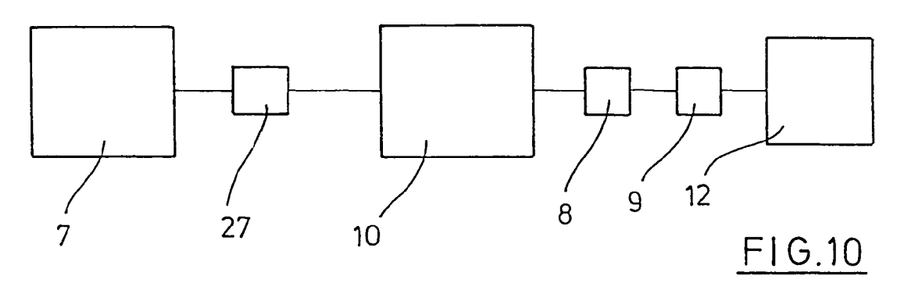
FIG. 10 shows another modification.

In the modification shown in FIG. 10, only the discharge system 27 is arranged between the ventilator 7 and the respiratory gas hose 10, and both the volume flow sensor 9 and the pressure sensor 8 are positioned between the respiratory gas hose 10 and the ventilation mask 12.

Figure 11:
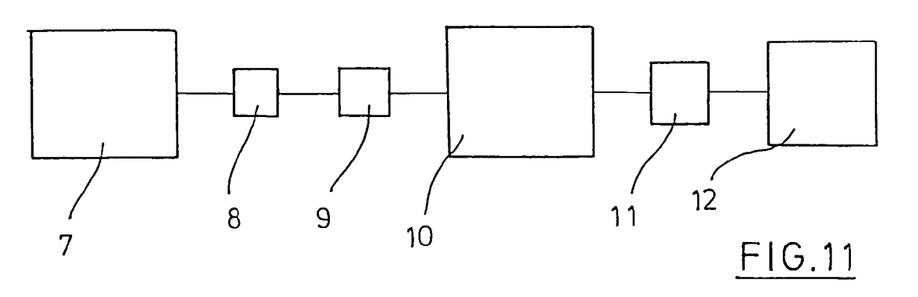
FIG. 11 shows another modification.

In the modification shown in FIG. 11, both the pressure sensor 8 and the volume flow sensor 9 are positioned between the ventilator 7 and the respiratory gas hose 10, and the expiration valve 11 is positioned between the respiratory gas hose 10 and the ventilation mask 12.

Figure 12:
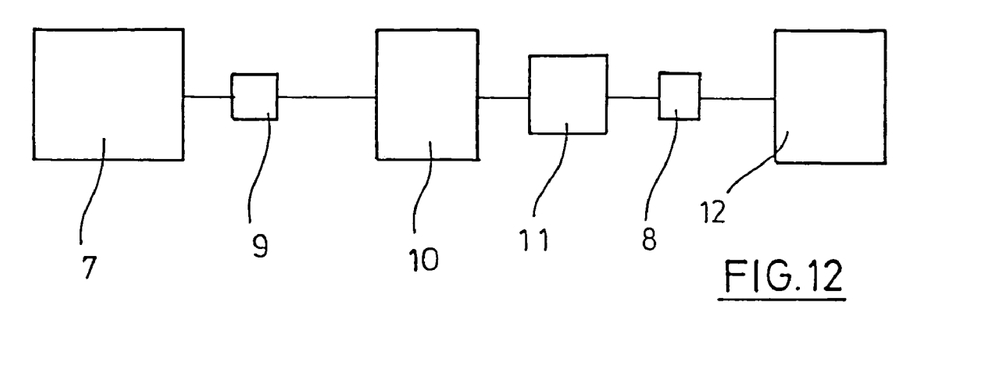
FIG. 12 shows another modification.

In the embodiment shown in FIG. 12, only the volume flow sensor 9 is arranged between the ventilator 7 and the respiratory gas hose 10, and the expiration valve 11 and the pressure sensor 8 are positioned between the respiratory gas hose 10 and the ventilation mask 12.

Figure 13:
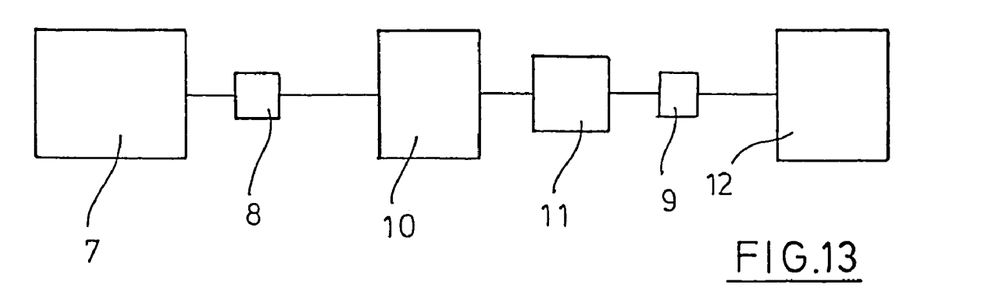
FIG. 13 shows another modified embodiment.

In the embodiment shown in FIG. 13, only the pressure sensor 8 is located between the ventilator 7 and the respiratory gas hose 10, and both the expiration valve 11 and the volume flow sensor 9 are located between the respiratory gas hose 10 and the ventilation mask 12.

Figure 14:
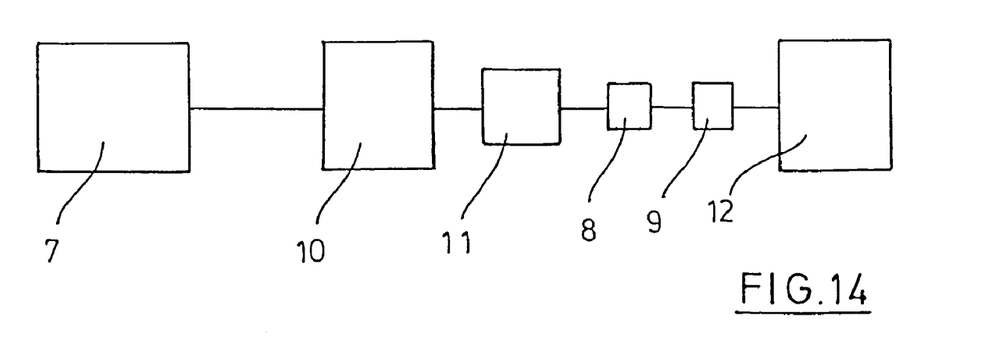
FIG. 14 shows another modified embodiment.

Finally, FIG. 14 shows an embodiment in which the ventilator 7 is directly coupled with the respiratory gas hose 10, and the expiration valve 11 and both the pressure sensor 8 and the volume flow sensor 9 are positioned between the respiratory gas hose 10 and the ventilation mask 12.

Figure 15:
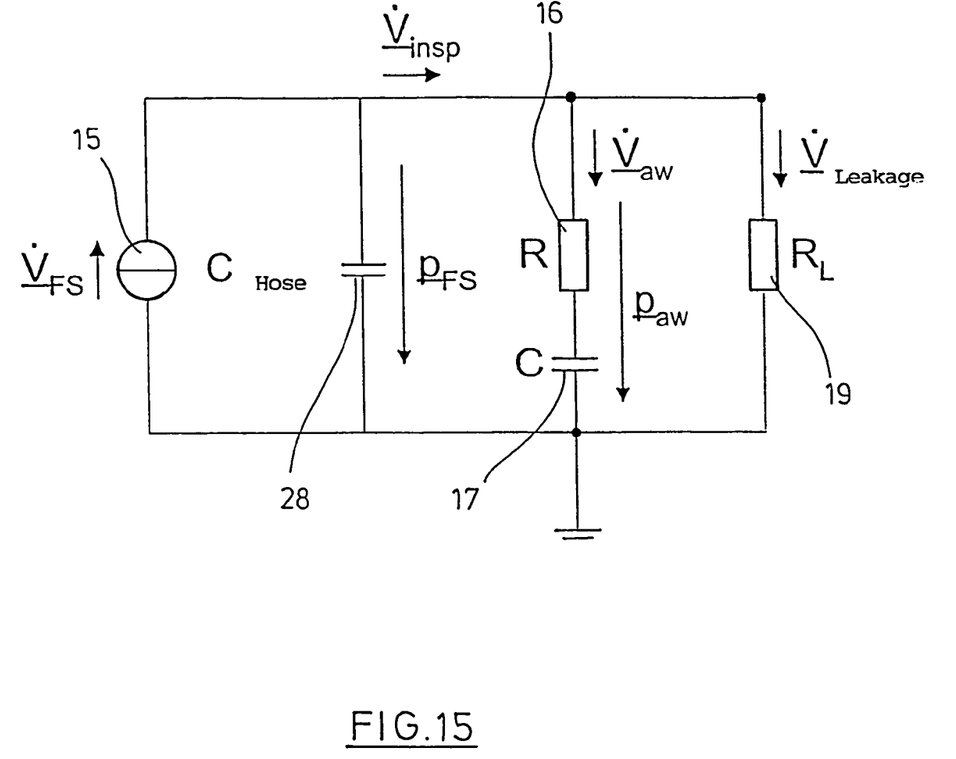
FIG. 15 shows an equivalent circuit diagram that has been modified from the diagram in FIG. 2.

FIG. 15 shows an equivalent circuit diagram that is supplemented relative to the diagram in FIG. 2 and is used in the case of linear behavior of the system comprising the patient and the respiratory gas hose. In an additional branch, the capacity 28 resulting from the volume of the hose is taken into consideration.

For the relationship between the measured data for flow $V'_{FS}$ and pressure $p_{FS}$ in the device, the transfer function corresponding to the following equation is obtained from the equivalent circuit diagram in the complex variable domain of the Laplace transform, neglecting a PEEP (positive end-expiratory pressure):

$$P_{FS}(s)/V'_{FS}(s)=(R_L \times (1+sRC))/(1+s(RC+R_L C+R_L C_s)+s^2 RCR_L C_s)$$

In this regard, the transit time behavior of the pressure inside the hose was disregarded ($P_{FS}=P_{aw}$), and $R_L$ was adopted as the leak resistance.

After a time discretization of this equation with a zero-order hold ($s \to (1-z^{-1})/T$), with the discrete-time shift operator $z^{-1}$, and with the sampling time T, the following representation of the relationship between the sequences of values $P_{FS,k}$ and $V'_{FS,k}$ is obtained:

$$P_{FS,k}/V'_{FS,k}=(b_0+b_1 Z^{-1})/(1+a_1 Z^1+a_2 Z^2)$$

where
$b_0=R_L T(T+RC)/K$
$b_1=-RCR_L T/K$
$a_1=(-T(RC+R_L C+R_L C_s)-2RCR_L C_s)/K$
$a_2=RCR_L C_s/K$
$K=T^2+T(RC+R_L C+R_L C_s)+RCR_L C_s$ If we now consider the conditions on the patient side of the respiratory gas hose, the following transfer function between $V'_{insp}$ and $P_{aw}$ is obtained:

$$P_{aw}(s)/V'_{insp}(s)=R_L \times (1+sRC)/(1+s(R+R_L)+C)$$

$$P_{aw,k}/V'_{insp,k}=(b_0+b_1 z^1)/(1+a_1 z^1)$$

where
$b_0=R_L(T+RC)/L$
$b_1=-R_L RC/L$
$a_1=-(R+R_L)C/L$
$L=T+(R+R_L)C$

If the transit time of the air pressure through the respiratory gas hose is taken into account, then $P_{FS}$ is not equal to $P_{aw}$. For pressure sensors on the device side, the expansion with $$P_{FS}(s)=P_{aw}(s)/(1+sT_s \times e^{sT_t})$$

can be used, in which $T_s$ is the integral-action time of the flexible respiratory gas hose with the hose connector. The delay time Tt corresponds to the sound transit time through the hose.

A higher degree of accuracy of the models in the above equations can be used to take into account such effects as gas compressibility. More precise formulations can also be used in the transition to the discrete-time representation.

The parameters R, C, and $R_L$ can be estimated by well-known identification and parameter estimation methods for linear as well as nonlinear systems. Especially a time-distributed computation of the parameter estimation is advantageous for implementation. In this regard, recursive methods make it possible to obtain results with the greatest time proximity to the last observation period.

The invention claimed is:

1. Method for detecting leaks in respiratory gas supply systems, in which both the pressure of the respiratory gas and the volume flow of the respiratory gas are detected and fed into an evaluation unit, wherein the respiratory quantities pressure and flow are recorded by the evaluation unit for at least two successive respiratory cycles, that at least one control parameter with different signal amplitudes is preset for successive respiratory cycles, and that resistance, compliance, and leak resistance are determined by a computation based on differential curves of pressure and flow for these respiratory cycles.

2. Method in accordance with claim 1, wherein the computation is performed for at least two immediately successive respiratory cycles.

3. Method in accordance with claim 1, wherein the computation is performed for at least two respiratory cycles that are separated by at least one other respiratory cycle.

4. Method in accordance with claim 1, wherein first and second pressure levels are preset for the successive inspirations.

5. Method in accordance with claim 4, wherein the first pressure level is selected higher than the second pressure level.

6. Method in accordance with claim 4, wherein the first pressure level is selected lower than the second pressure level.

7. Method in accordance with claim 1, wherein first and second volume flows are preset for the successive respiratory cycles.

8. Method in accordance with claim 7, wherein the first volume flow is preset higher than the second volume flow.

9. Method in accordance with claim 7, wherein the first volume flow is preset lower than the second volume flow.

10. Method in accordance with claim 1, wherein a large number of respiratory cycles, each with a varied control parameter, are carried out in such a way that the values of the control parameters are statistically distributed in such a way that a mean value corresponds to a preset desired value for the control parameter.

11. Method in accordance with claim 1, wherein a leak compensation is carried out.

12. Method in accordance with claim 11, wherein the leak compensation is carried out dynamically.

13. Method in accordance with claim 1, wherein a determination of spontaneous respiratory behavior is performed by the evaluation unit (14).

14. Method in accordance with claim 1, wherein the evaluation unit (14) compensates the effects of spontaneous respiratory behavior.

15. Method in accordance with claim 1, wherein leak detection is carried out in an area between a ventilator (7) and a patient (13).

16. Method in accordance with claim 1, wherein measurements are carried out only during inspiratory phases of the respiratory cycles.

17. Device for detecting leaks in respiratory gas supply systems, comprising a device for detecting the pressure of a respiratory gas and a device for detecting the volume flow of the respiratory gas, wherein the detection devices are connected to an evaluation unit, wherein the evaluation unit (14) is configured to determine the respiratory quantities pressure and flow, further comprising a storage device for at least one pair of value sequences of pressure and flow for a respiratory cycle, and means for generating at least one differential sequence for determining differential curves of compliance and resistance for at least two successive respiratory cycles.

18. Device in accordance with claim 17, wherein at least one pressure sensor (8) is connected to the evaluation unit (14).

19. Device in accordance with claim 17, wherein at least one volume flow sensor (9) is connected to the evaluation unit (14).

20. Device in accordance with claim 17, wherein at least one of the sensors (7, 8) is arranged so that it faces a ventilator (7) that is supplying the respiratory gas.

21. Device in accordance with claim 17, wherein one of the sensors (8, 9) is arranged so that it faces a ventilation mask (12).

22. Device in accordance with claim 17, wherein an expiration valve (11) is arranged so that it faces the ventilation mask (12).

23. Device in accordance with claim 17, wherein a discharge system (27) is arranged so that it faces the ventilation mask (12).

24. Device in accordance with claim 17, wherein a discharge system (27) is arranged so that it faces the ventilator (7).

25. Device in accordance with claim 17, wherein an expiration valve (11) is arranged so that it faces the ventilator (7).

26. Device in accordance with claim 17, wherein a patient interface that is connected with the ventilator (7) by the respiratory gas hose (10) is designed as an invasive device.

27. Device in accordance with claim 17, wherein a patient interface that is connected with the ventilator (7) by the respiratory gas hose (10) is a noninvasive device.

28. Device in accordance with claim 17, wherein the evaluation unit (14) has an amplitude generator for a pressure that varies from respiratory cycle to respiratory cycle.

29. Device in accordance with claim 17, wherein the evaluation unit (14) has an amplitude generator for a volume flow that varies from respiratory cycle to respiratory cycle.

* * * * *